(12) United States Patent
Haas et al.

(10) Patent No.: US 8,950,934 B2
(45) Date of Patent: Feb. 10, 2015

(54) DEVICE FOR MEASURING THE FLASH POINT OF LIQUIDS AND SOLIDS

(75) Inventors: Nicolas Haas, Hohenruppersdorf (AT); Klaus Hense, Traiskirchen (AT)

(73) Assignee: Grabner Instruments Messtechnik GmbH, Vienna (AT)

( * ) Notice: Subject to any disclaimer, the term of this patent is extended or adjusted under 35 U.S.C. 154(b) by 259 days.

(21) Appl. No.: 13/697,047

(22) PCT Filed: May 10, 2011

(86) PCT No.: PCT/AT2011/000220
§ 371 (c)(1), (2), (4) Date: Nov. 29, 2012

(87) PCT Pub. No.: WO2011/140576
PCT Pub. Date: Nov. 17, 2011

(65) Prior Publication Data
US 2013/0136150 A1    May 30, 2013

(30) Foreign Application Priority Data

May 11, 2010 (AT) .................... A 797/2010

(51) Int. Cl.
*G01N 25/00* (2006.01)
*G01K 1/00* (2006.01)
*G01N 25/52* (2006.01)
*G01N 25/50* (2006.01)

(52) U.S. Cl.
CPC .............. *G01N 25/52* (2013.01); *G01N 25/50* (2013.01)
USPC .................. 374/8; 374/208; 374/143

(58) Field of Classification Search
USPC .............................. 374/8, 143, 208
See application file for complete search history.

(56) References Cited

U.S. PATENT DOCUMENTS

| | | | | |
|---|---|---|---|---|
| 4,549,815 A | * | 10/1985 | Venkat et al. | 374/8 |
| 5,176,449 A | | 1/1993 | Grabner | |
| 5,182,940 A | * | 2/1993 | Bailey et al. | 73/36 |
| 5,322,360 A | * | 6/1994 | Willis et al. | 374/38 |
| 5,869,343 A | * | 2/1999 | Handschuck et al. | 436/143 |
| 2011/0228808 A1 | * | 9/2011 | Ayotte et al. | 374/8 |

FOREIGN PATENT DOCUMENTS

EP    0 486 980 A1    5/1992

OTHER PUBLICATIONS

Walter Herzog GMBH Automated Closed Cup Flash Point Analyzers HFP 36x Series, pp. 1-4.
James Colotti EMC Design Fundamentals, XP55002904, http://www.ieee.li/dpf/viewgraphs/emc_design_fundamentals.pdf, pp. 1-69, (2005).
EMI, RFI, and Shielding Concepts, MT-095 Tutorial, XP55002897, http://www.analog.com/static/imported-files/tutorials/MT-095.pdf, pp. 1-16, (2009).
Stutzman, Definition, 1.5 Radiation Pattern, pp. 17-32 (1981).

* cited by examiner

*Primary Examiner* — Mirellys Jagan
(74) *Attorney, Agent, or Firm* — Fitch, Tabin & Flannery LLP (57) ABSTRACT

Device for measuring the flash point of liquids and solids includes a measurement chamber (formed by a measurement basin and a lid) and which is provided with means for heating the liquid or the solid in the basin, an electrical igniter having a spark gap, temperature sensors, a pressure measuring apparatus and a press-on device for tightly connecting the measurement basin and the lid. A control device is provided in order to control the heating means, the igniter and the press-on device and to collect the measured values of the temperature sensors and the pressure measuring apparatus. The control device is formed by a computer designed as an embedded system, which is connected to the heating means, the igniter, the press-on device, the temperature sensors and the pressure measuring apparatus by means of an interface device. The measurement chamber and the control device are arranged in a common housing.

20 Claims, 5 Drawing Sheets

DEVICE FOR MEASURING THE FLASH POINT OF LIQUIDS AND SOLIDS

CROSS-REFERENCE TO RELATED APPLICATIONS

This Application is a U.S. National Stage Application filed under 35 U.S.C. §371 of International Application PCT/AT2011/000220, filed May 10, 2011, designating the United States, which claims priority from Austrian Patent Application A 797/2010, filed May 11, 2010, the complete disclosures of which are hereby incorporated herein by reference in their entirety for all purposes.

BACKGROUND OF THE INVENTION

The invention relates to a device for measuring the flash point of liquids and solids in a measurement chamber, which is formed by a measurement basin and a lid and which is provided with means for heating the liquid or the solid in the measurement basin, an electrical igniter having a spark gap, temperature sensors, a pressure measuring apparatus, and a press-on device for tightly connecting the measurement basin and the lid, a control device also being provided in order to control the heating means, the igniter and the press-on device and to collect the measured values of the temperature sensors and of the pressure measuring apparatus.

Such a device has become known for example from EP 486 980 B1. The flash point of a liquid or of a solid is ascertained in such a way that the substance to be investigated is first put into a heatable measurement chamber, and the ascertainment of a flame generation, which is carried out in order to determine the flash point, takes place by measuring the pressure present in the measurement chamber after an ignition, said pressure increasing when the substance to be investigated ignites as a result of the temperature increase brought about by the flame in the measurement chamber.

The flash point of a substance is used in transport and safety regulations in order to define inflammable and explosive materials and to provide information concerning the presence of highly volatile and flammable components in a low-volatility and non-flammable substance.

According to ASTM, the flash point is defined as the lowest temperature, corrected to a barometric air pressure of 101.3 kPa, at which the vapour of the sample ignites as a result of the application of a test flame, wherein a flame arises which itself wanders over the surface of the sample and covers at least two thirds of the surface.

The flash point of a substance is ascertained under laboratory conditions with exposure to air.

A number of measurement methods recognised by the ASTM and ISO exist worldwide for measuring the flash point. Use is always made of a sample vessel, which is heated by flame or electrically. The open sample vessel is hardly any longer admissible for test measurements, since the highly volatile components evaporate and can no longer contribute to the combustion.

In the case of the method known from EP 486 980 B1, the procedure is such that the substance to be measured, mainly a liquid, is filled into the measurement basin in a predetermined quantity. The measurement basin is pressed against the heatable lid either manually or automatically.

The measurement procedure is started by the lid being heated to a predetermined temperature which is reliably below the expected flash point temperature. The monitoring and measurement of the temperature takes place by means of a temperature sensor.

As a result of the temperature contact of the measurement basin with the lid, the basin is also heated. However, its temperature remains below the temperature of the lid.

After a waiting time for the temperature equalisation of the measurement basin and the lid, the temperature of the lid is slowly increased further and an ignition by means of electrodes is carried out at constant temperature intervals. Immediately after the ignition, the rise in pressure is measured in the measurement chamber by means of a pressure measuring apparatus, which is preferably constituted as a piezoresistive pressure sensor. The flash point temperature is indicated by a further temperature sensor. The measurement chamber is defined by the measurement vessel or the volume of the substance to be measured and the free space under the lid.

BRIEF SUMMARY OF THE INVENTION

In order to be able to carry out the method automatically and to deliver precise and reproducible measurement results, a suitable control device must be provided in order to control the heating means, the igniter and the press-on device and to collect the measured values of the temperature sensors and of the pressure measuring apparatus. Such control devices are usually constituted by simple and robust microcontrollers or microprocessors. The simplicity and robustness is for the most part, but not exclusively, characterised by the following features:
1) the clock frequency of the processor amounts to 20 MHz or less
2) the components used in the control device are operated with relatively high voltages typically of 5V or 3.3 V and
3) the integration of the components is very low, the control therefore having a low number of semiconductors per unit area.

An example of a previously used microprocessor for such a control is the H8/510 microprocessor from the firm Hitachi Semiconductor.

On account of these properties, the program run with this kind of control can however be changed only to a limited extent, adaptations by the user being very difficult and limited.

In modern flash point measurement devices, which are intended to be used for a large number of different liquids and solids and which are intended to deliver reliable and reproducible measurement results under the most diverse ambient conditions, the program run has to be adapted to the given circumstances and, if need be, even case by case, and the control depends in particular on different parameters which, as the case may be, require a corresponding user input.

The more complex control tasks required for this were only able to be managed with the aid of an external operating and control computer in the case of flash point measurement devices. It is true that the connection of such external operating and control computers usually took place by means of standardised interfaces, so that conventional computers (PCs) could be used. However, the use of an external control and operating computer is connected with considerable drawbacks, since the use of the flash point measurement device was always dependent on the location of the given external control and operating computer. The use of an external control does however have the advantage that the high temperatures which prevail in the region of the ignition source of the flash point measurement device, and in particular also the strong electromagnetic field which emerges from the ignition source, do not have any negative influences on the control device on account of the external arrangement, so that such an external control can be regarded as particularly interference-proof and fail-safe.

The present invention aims to develop a flash point measurement device of the type mentioned at the outset, in such a way that an external control can be dispensed with, in doing so the ease of operation is intended to increase at the same time. This is intended to be achieved without the size of the flash point measurement device and the susceptibility to failure being significantly increased. At the same time, more complex control tasks should be managed and, in particular, a flexible adaptation of the program run should be possible, and also the possibility of being able to exchange the components of the controls in a straightforward manner should be guaranteed.

To solve this problem, the device of the kind mentioned at the outset is essentially developed in such a way that the control device is formed by a computer designed as an embedded system, in particular an embedded PC, which is connected to the heating means, the igniter, the press-on device, the temperature sensors and the pressure measuring apparatus by means of an interface device, and that the measurement chamber and the control device are arranged in a common housing. Through the use of a computer designed as an embedded system, in particular an embedded PC, the possibility of a space-saving arrangement of the control in the housing of the flash point measurement device is created, wherein use may be made of tried and tested and standardised components. As a result of the fact that the embedded system is connected to the heating means, the igniter, the press-on device, the temperature sensors and the pressure measuring apparatus by means of an interface device, a straightforward exchange of the control is enabled, since the embedded system, which is usually accommodated on a single printed circuit board, merely has to be connected to the interface device. The embedded system is preferably accommodated detachably in the interface device and is characterised, for example, in that a plug strip or contact strip can be inserted into a corresponding socket of the interface device with counter-contacts or counter-plugs. The interface device can for example contain the driver components and the software for controlling the individual hardware components of the flash point measurement device. Overall, therefore, a modular architecture is created, wherein the individual components and in particular the embedded system can be exchanged in a straightforward manner, this being advisable especially for upgrades. Moreover, through the use of standardised components, the production and development of these components can easily be handled by third parties.

Within the scope of the invention, an embedded system is understood to mean an electronic computer or a computer which is embedded in a technical context. The embedded system can be based on similar hardware to office computers, so that the programming can take place using familiar and tried and tested development environments. Embedded PCs usually even comprise a completely standard PC architecture, wherein the general availability of corresponding PC software and of development environments can be used. The electronics of an embedded system are usually formed by a microprocessor with corresponding peripherals or by a microcontroller. Embedded systems are particularly low-cost and can be installed in an extremely small space. Embedded systems usually comprise a basic CPU module with a power supply unit, system interfaces such as for example RS232, USB or Ethernet, a bus terminal and an embedded PC operating system.

The boundary between a high-performance embedded system and an embedded PC is becoming increasingly blurred, since numerous components are already available on the market which can be regarded not directly as a conventional PC configuration, since several interfaces are already provided for the control of peripheral devices which are not used in an office computer. Nonetheless, the capacity of such components is perfectly compatible with those of a PC. In addition, the programming of these components is possible in the usual PC environment on account of the embedded PC operating system used. Due to the increased capacity of these embedded systems and embedded PCs, their susceptibility to failure (higher clock frequency, lower voltage, higher integration) is markedly increased. Embedded systems whose computing power can be compared with that of a conventional PC are therefore preferably regarded as embedded systems within the meaning of the invention. In particular, these are systems which have a clock frequency of more than 100 MHz or a supply voltage of less than 3.3 V or a high integration of the components (e.g. ARM 9, XSCALE or comparable or power amplifiers) or an operating system related to an embedded PC operating system.

Since the flash point measurement device according to the invention manages without an external control device, it is advantageous if the user inputs required for the operation can also be carried out directly on the flash point measurement device. In this connection, the invention preferably makes provision such that the computer can be operated with the aid of a touch-sensitive display device, in particular a display screen. Such touch-sensitive display screens offer improved display options and increased operator comfort. On account of the strong electromagnetic fields which emerge from the ignition source arranged in the device, however, measures should be taken to prevent disruptions to the display. In this connection, a preferred embodiment makes provision such that the electrical connection of the display device to the computer is constituted as an analog connection. It has in fact been shown that digital connections, such as for example HDMI, reveal a failure of communication during the ignition. On account of the provided digital log, the regeneration of the digital connection takes much longer than in the case of an analog communication, where any occurring disruptions can occur for the period of the pulse length (max. 90 ms), which however cannot be perceived by the human eye.

In computers designed as embedded systems, use is usually made of components which are sensitive to electromagnetic fields. It is therefore advantageous to protect and shield such sensitive electronic components accordingly, in order to guarantee operating reliability even when the computer is arranged relatively close to the ignition source to reduce the size of the flash point measurement device. The susceptibility to failure of the electronic components, moreover, increases markedly with increasing miniaturisation, so that more powerful devices are more markedly endangered than older and slower microcontrollers. Within the scope of the invention, the most diverse measures are proposed for protecting the electronic components of the computer against magnetic fields, the measures being able to be used both separately from one another as well as jointly.

The invention is preferably developed such that electronic components of the computer sensitive to electromagnetic fields lie inside a region of a cone defined by a lower and an upper opening angle, the axis of said cone lying in the extension of the spark gap.

The property of importance for the risk of a crash is the energy density of the irradiated field at the site of the most sensitive components. Sensitive components are considered in particular to be analog-to-digital converters, operational amplifiers and any microcontroller (CPU). Irradiated power density $P_A$ can be calculated for example with the Poynting vector and, for an electric dipole (to which the spark can be approximated to a good approximation), is proportional to $$P_A \propto \sin^2(\theta)$$

An additional reduction in the power density can be achieved by suitable orientation of the printed circuit board, the scalar product of the Poynting vector with the surface normal of the printed circuit board being of importance here. The minimum power density is achieved by a vertical orientation of the Poynting vector to the surface normal. The irradiated power density thus works out at $$P_E = P_A \cos(\theta) \propto \sin^2(\theta)\cos(\theta)$$

Two optimum regions result from this in a conical region of 0°-40° (preferably 0°-20°) and 70°-90° (preferably 84°-90°) (on the assumption that the surface normal of the printed circuit board runs parallel to the spark direction). If the surface normal lies normal to the spark direction, the optimum cone lies only in the lower angular range of 0°-30°; technical drawbacks arise here, however, on account of the much larger design. The axis of rotation of the cone is always formed by the direction of the spark.

In addition to (or as an alternative to) the arrangement of the printed circuit board or the sensitive component in the shadow region, a protection can be achieved by the fact that electronic components of the computer sensitive to electromagnetic fields are arranged inside a shield constituted in the manner of a Faraday cage. An at least 0.5 mm thick steel plate is preferred as a shield. An improvement to the shielding can be achieved by greater material thicknesses, and/or better-conducting materials (copper, aluminium or others). It is preferable for none of the aforementioned sensitive components to be subjected to direct irradiation. Any necessary cable lead-throughs are therefore advantageously arranged such that they do not point directly in the direction of the spark, in particular are arranged on the side facing away. The thereby lengthened cable runs must be accepted consciously. Irradiation via the cables can be minimised by a technically standard arrangement of buried cables in the case of multi-conductor connections.

If, however, openings in the shielding are required on the side facing the spark (insofar as the latter are located in the critical region, because it is not shielded), provision is preferably made such that electronic components of the computer sensitive to electromagnetic fields are arranged outside the region of a cone with an opening angle of 30°, whose axis runs normal to the perforation and whose cone generatrices proceed from the edge of the perforation. The opening angle 30° results as follows: due to diffraction and electron plasma resonance in the conducting material, the perforation in the shielding itself becomes a source of electromagnetic radiation, wherein the vector of the dipole moment lies in the plane of the shielding and itself again represents a dipole-like irradiation characteristic with a "spark shadow" in a cone around the vector of the dipole moment. Since, however, the vector of the induced dipole moment can be estimated only insufficiently, i.e. the latter is orientated arbitrarily in the hole, a conical region normal to the shielding results. The opening angle of this cone corresponds to the complementary angle of the aforementioned range and would therefore lie at approximately 60° (optimally less than (80°). Since the arising dipole moment is however much smaller than the primary moment of the spark, the margin of commutation can be reduced and results at approximately 30°.

In order to further increase the reliability against disruption, provision is preferably made such that the current supply unit of the igniter and the current supply unit of a printed circuit board with the electronic components of the computer sensitive to electromagnetic fields are separated galvanically from one another. The embodiment is advantageously provided such that the current supply units galvanically separated from one another are supplied by a common mains supply.

Moreover, it has turned out to be favourable for storage media of the computer to be constituted as solid-state drives. Such solid-state drives do not comprise any moving parts, such as for example motors or positioning mechanisms for reading arms, which are very sensitive to electromagnetic fields. Furthermore, this prevents a data loss due to a demagnetised transient field.

In order to increase the measurement accuracy of the flash point determination and in order to achieve good reproducibility, provision is also preferably made such that the means for heating the liquid or the solid comprise means for heating the lid and the measurement basin which can be pressed onto the lid from beneath has a temperature which is necessarily lower than the temperature of the lid. The heatable lid is preferably provided with the electrical igniter, the pressure measuring apparatus and two temperature sensors for the lid and the contents of the measurement chamber respectively, and the measurement basin is arranged so that it can be removed from the lid for emptying, cleaning and filling. The pressure measuring apparatus is preferably constituted as a piezoresistive pressure sensor in a manner known per se.

It is an essential advantage of this embodiment that the measured pressure increase is not only dependent on the temperature of the burnt gas, but also on the volume of the flame. The volumetric magnitude of the flame can thus be acquired by adjusting a threshold for the pressure increase.

BRIEF DESCRIPTION OF THE DRAWINGS

The invention is explained in detail below with the aid of an example of embodiment represented diagrammatically in the drawing. In the latter.

DETAILED DESCRIPTION OF THE INVENTION

Figure 1:
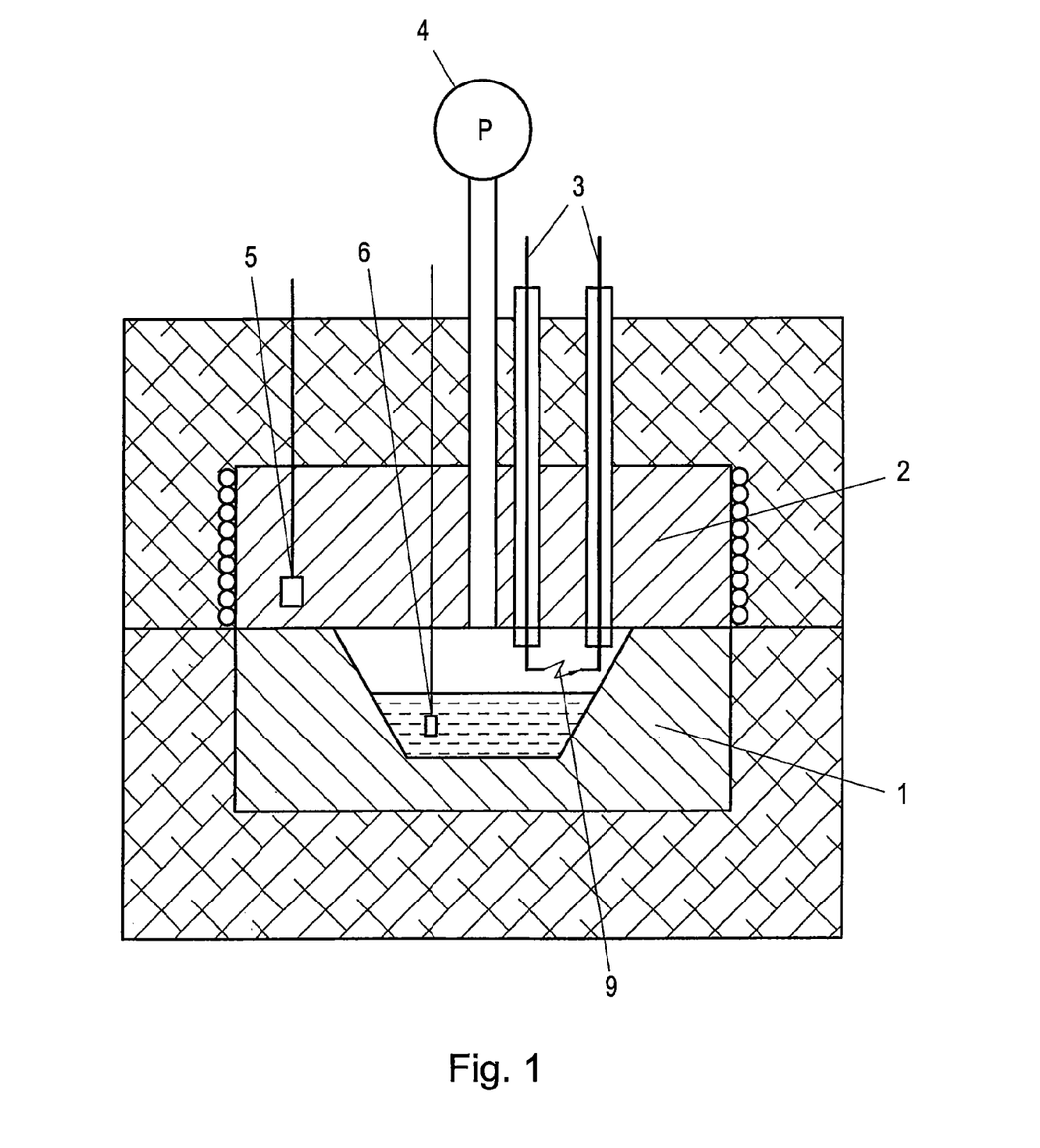
FIG. 1 shows diagrammatically a detail of the device according to the invention in the region of the measurement chamber.

FIG. 1 represents a measurement basin 1 and a lid 2, which are produced from aluminium for the purpose of good heat conduction. The temperature measurement and control takes place by means of a temperature sensor 5 which has a good thermal coupling with the lid. Located in electrically heated lid 2, which is installed fixedly in the device so as to be thermally insulated, are two electrodes 3 for the electrical ignition. The ignition tips of the electrodes are located approx. 2 mm above the surface of the substance to be measured. The ignition spark is electrically generated with a commercially available ignition coil. Furthermore, a second temperature sensor 6, which projects directly into the substance to be measured, is installed in lid 2. The temperature of the substance to be measured is thus detected precisely and is then deemed to be a measured value for the flash point.

The main purpose of the measurement device is the detection of the flash point. It is assumed that any combustion is associated with an increase in temperature. In contrast with the conventionally used temperature measurement, the pressure increase as a result of the combustion temperature inside the measurement chamber is used. If a combustion temperature of approx. 1000° C. is assumed, the pressure increases with the same volume according to the gas equation.

$$p \times v/T = \text{const}$$

$$p2/p1 = T2/T1$$

p2 pressure at 1000° C.
p1 pressure at measurement temperature (101.3 kPa)
T2 absolute combustion temperature (1000+273)
T1 absolute measurement temperature (tm+273)

With a measurement temperature of 100° C., this corresponds to the pressure increase to approx. 350.0 kPa.

The preselected volume of burnt gas at high pressure is distributed over the whole gas volume in the measurement chamber. The actual pressure increase in the chamber can be ascertained therefrom. A correction of the required pressure increase via the measurement temperature is easily possible and also required for precise determinations.

On the assumption that the flame occupies 20% of the free gas volume, a final pressure increase of approx. 50 kPa results. This is a measured quantity which can be measured with great accuracy.

For the precise detection of the pressure increase, use is preferably made of a pressure measuring apparatus 4 which is constituted as a piezoresistive pressure sensor and which is connected via a hose line to the measurement chamber.

Figure 2:
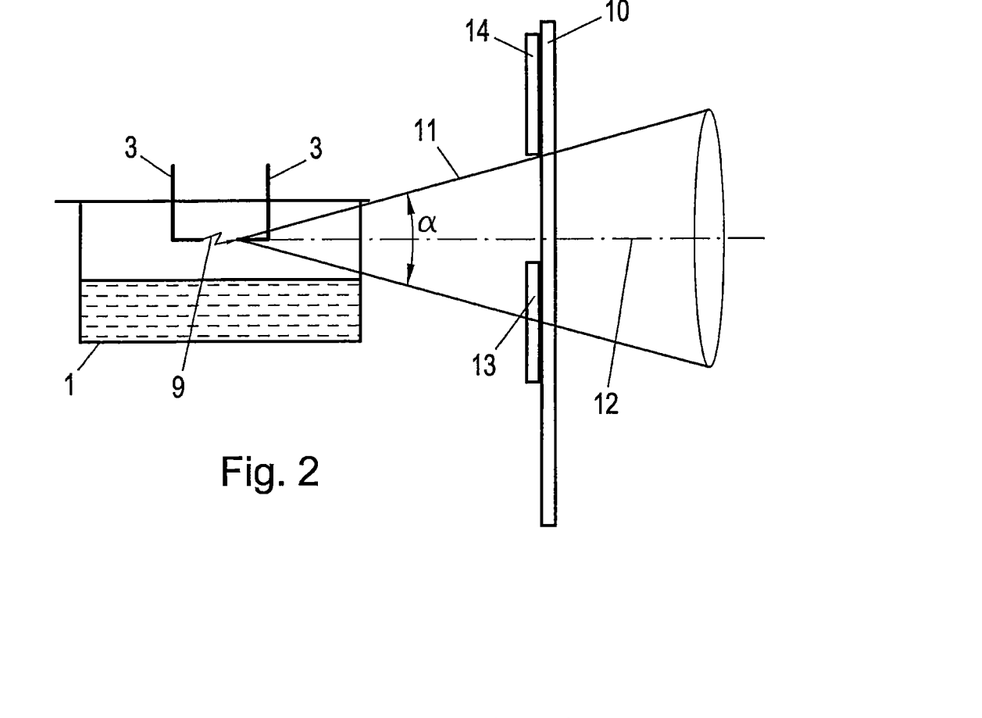
FIG. 2 shows diagrammatically the position of a printed circuit board of an embedded computer relative to the ignition source.

In FIG. 2, a measurement basin is again denoted by 1 and the spark gap formed between the two electrodes 3 is denoted by 9. Furthermore, a printed circuit board 10 of the embedded computer is represented, whose surface normal runs parallel to spark gap 9. In order to protect electronic components of printed circuit board 10 that are particularly sensitive to electromagnetic fields, said components can for example be arranged inside the cone denoted by 11. In the present case, the cone has an opening angle α of 30° and has an axis 12 lying in the extension of spark gap 9. The electromagnetic load arising from the ignition source is weaker inside the region of cone 11 than outside that cone, so that an electronic component 13 arranged inside this region is accordingly better protected than an electronic component 14 arranged outside this region.

Figure 3:
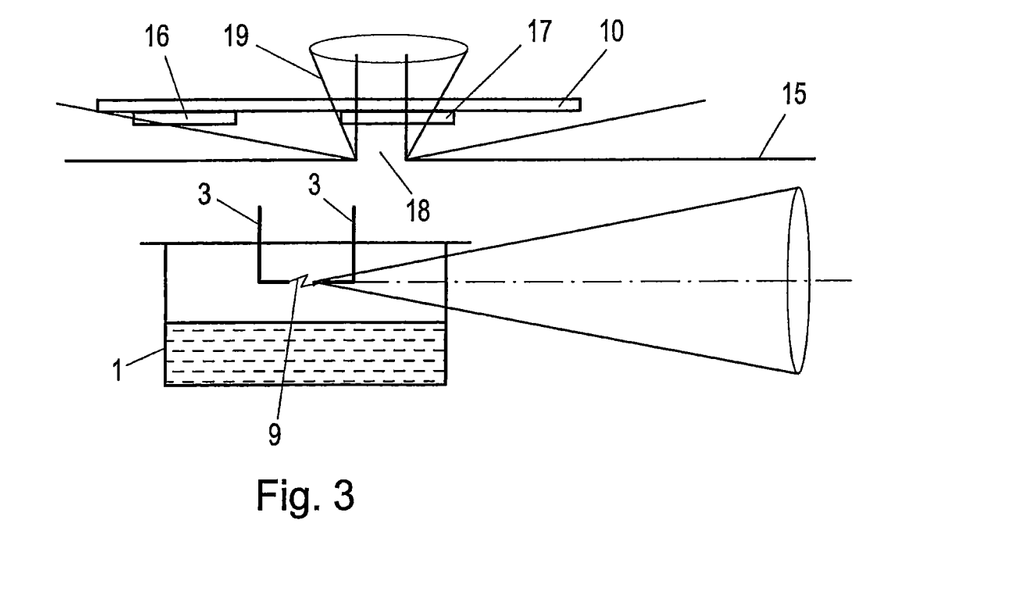
FIG. 3 shows the arrangement of a shield between the ignition source and a printed circuit board of the embedded computer.

FIG. 3 represents a modified embodiment, wherein printed circuit board 10 is arranged parallel to spark gap 9. Furthermore, a shield 15 constituted in the manner of a Faraday cage is represented, so that electronic components 16 and 17 are basically shielded. If, however, a perforation 18 has to be arranged in shield 15, for example to enable a cable lead-through, it is preferred for particularly sensitive electronic components to be arranged outside the cone denoted by 19.

Figure 4:
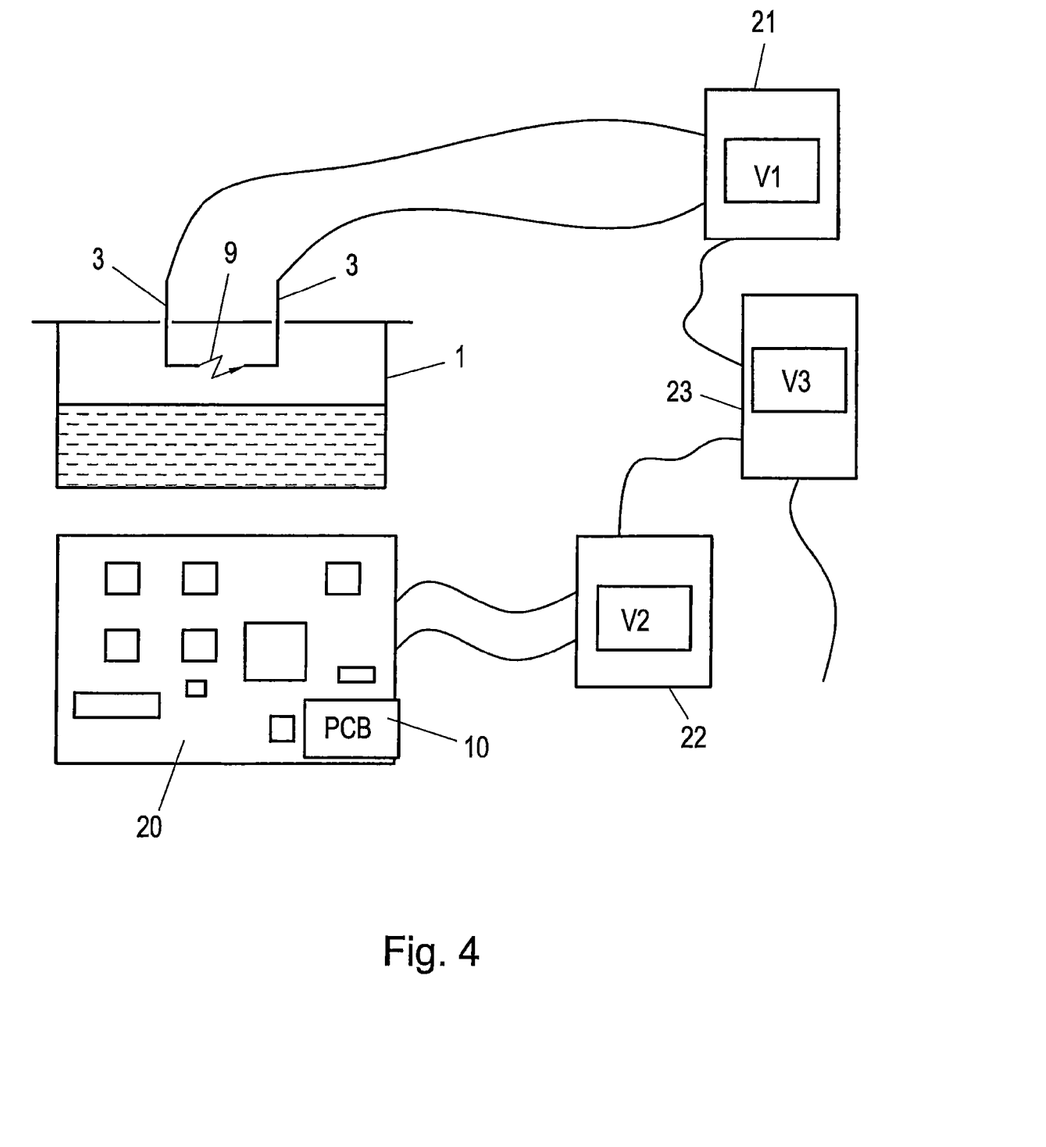
FIG. 4 shows a diagrammatic view of the current supply for the ignition source and the embedded system.

In FIG. 4, the measurement chamber is again denoted by 1, and an embedded system is also denoted schematically by 20. A printed circuit board of embedded system 20 is denoted schematically by 10. The supply of spark gap 9 takes place via a power supply unit 21. The supply of the CPU of printed circuit board 10 takes place via a further power supply unit 22. Less sensitive printed circuit boards of the embedded system can certainly also be connected to power supply unit 21. Power supply units 21 and 22 are galvanically separated from one another and brought together via unit 23 onto a common mains supply.

Figure 5:
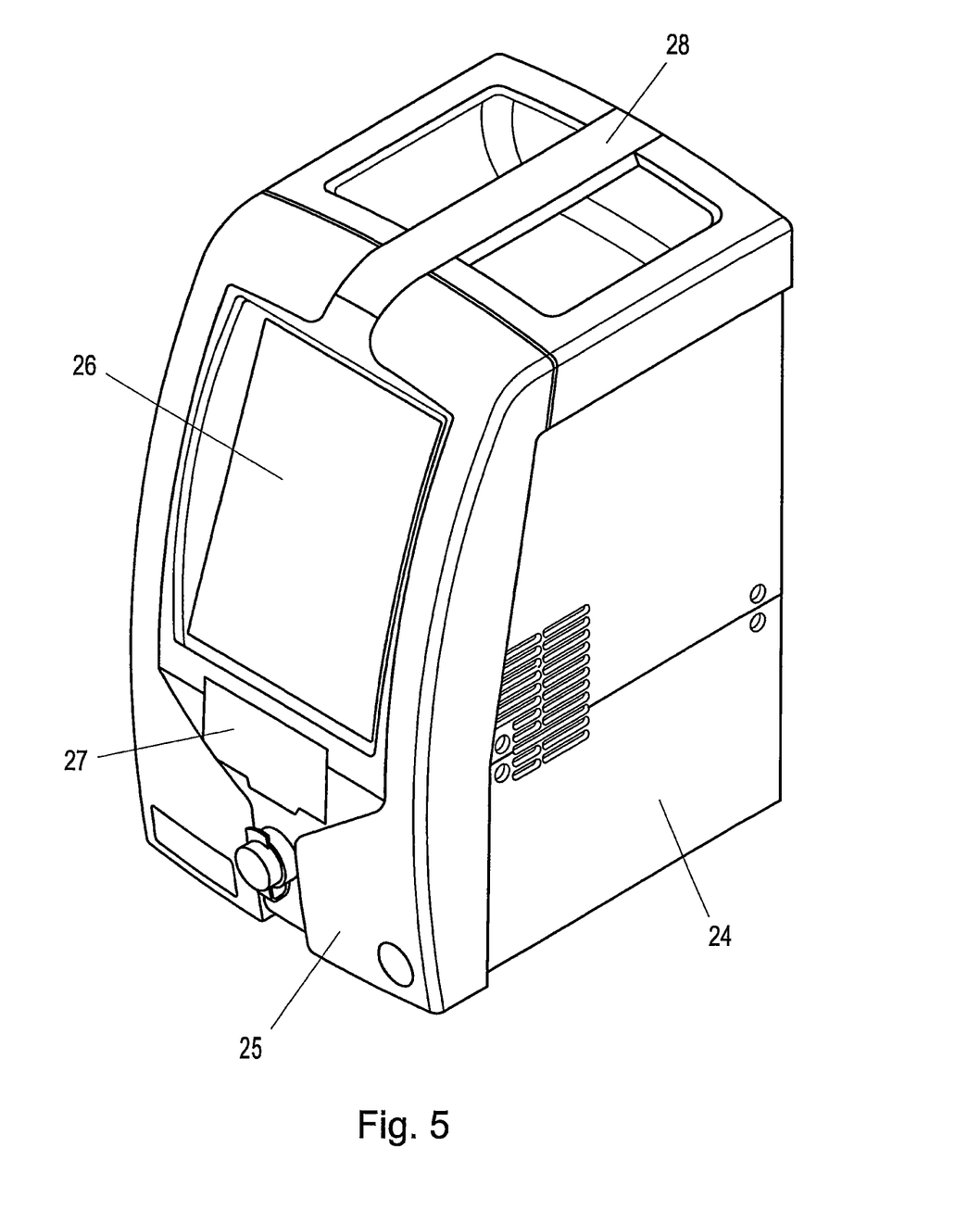
FIG. 5 shows an external view of the housing and FIG. 6 shows a view according to FIG. 5 with the housing represented partially broken open.

FIG. 5 shows housing 24 with a front cover 25, which comprises all the necessary operator controls. In particular, a touch-sensitive display device 26 as well as a closable access 27 for introducing and filling the measurement basin are provided. In order to facilitate transport, a carrying grip 28 is provided.

Figure 6:
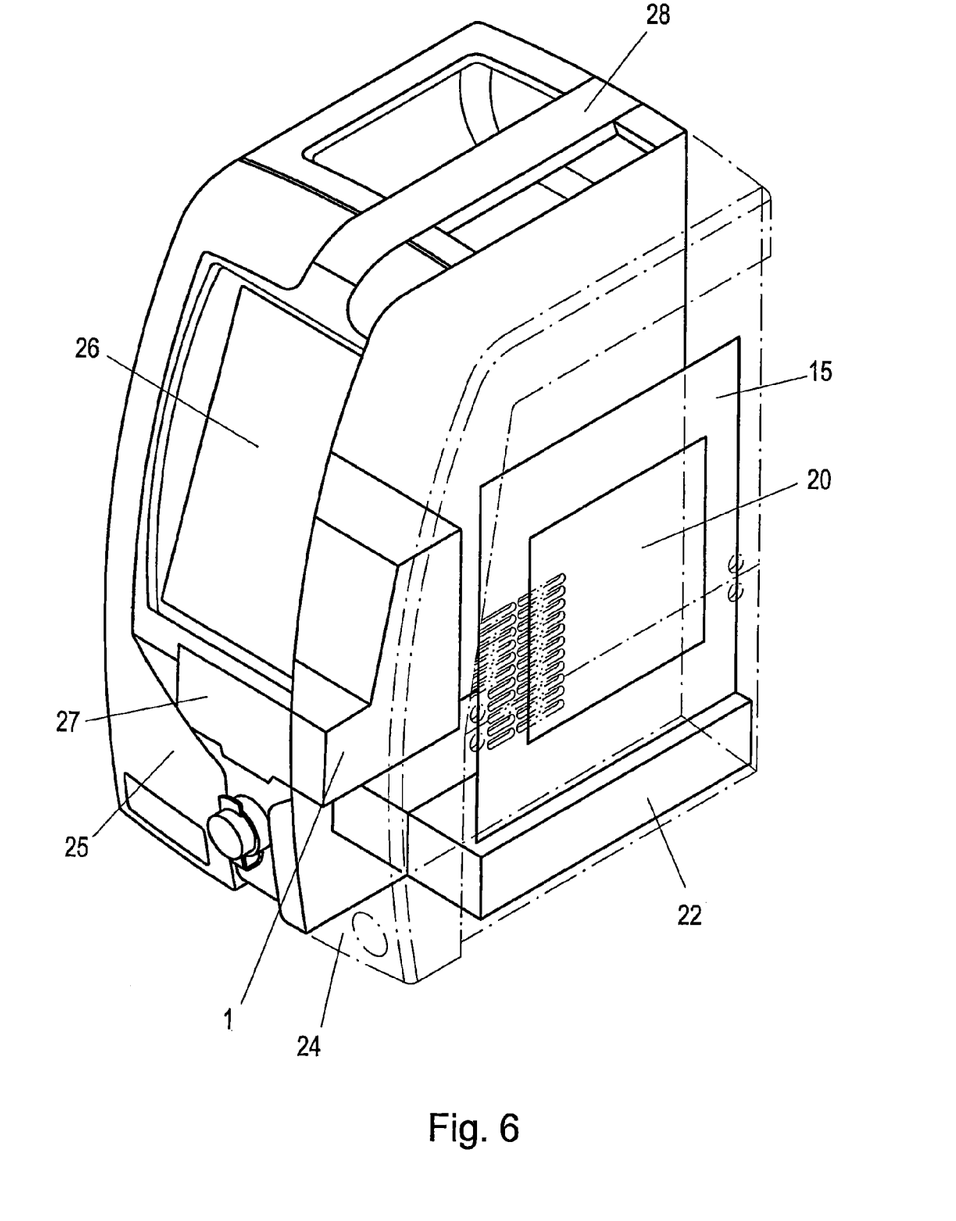

In the representation according to FIG. 6, the arrangement of measurement chamber 1 in the interior of housing 24 can be seen. Embedded system 20 extends essentially in a vertical plane and is shielded with the aid of a shield 15. The voltage supply for embedded system 20 is denoted by 22.

The invention claimed is:

1. A device for measuring the flash point of liquids and solids in a measurement chamber comprising a measurement basin and a lid to form the chamber; means for heating the liquid and/or the solid in the measurement basin; an electrical igniter having a spark gap; temperature sensors; a pressure measuring apparatus; a press-on device for tightly connecting the measurement basin and the lid; a control device in order to control the heating means, the igniter and the press-on device and to collect the measured values of the temperature sensors and of the pressure measuring apparatus, said control device comprising a computer as an embedded system; an interface device for connecting the computer to the heating means, the igniter, the press-on device, the temperature sensors and the pressure measuring apparatus; and a common housing wherein the measurement chamber and the control device are arranged in the common housing and the computer has components sensitive to electromagnetic fields arranged inside a region protected or shielded against electromagnetic fields and other components of the computer are arranged outside the region.

2. The device according to claim 1, wherein the storage media of the computer comprise solid-state drives.

3. The device according to claim 1, wherein the pressure measuring apparatus comprises a piezoresistive pressure sensor.

4. The device according to claim 1, wherein the touch-sensitive display device comprises a display screen.

5. The device according to claim 1, wherein the computer can be operated with the aid of a touch-sensitive display device.

6. The device according to claim 5, wherein the electrical connection of the display device to the computer is constituted as an analog connection.

7. The device according to claim 1, wherein the current supply unit of the igniter and the current supply unit of a printed circuit board with the electronic components of the computer sensitive to electromagnetic fields are galvanically separated from one another.

8. The device according to claim 7, wherein the current supply units galvanically separated from one another are supplied from a common mains supply.

9. The device according to claim 1, wherein the means for heating the liquid or the solid comprises means for heating the lid and the measurement basin which can be pressed onto the lid from beneath has a temperature which is necessarily lower than the temperature of the lid.

10. The device according to claim 9, wherein the heatable lid is provided with the electrical ignite, the pressure measuring apparatus and two temperatures sensors respectively for the lid and the contents of the measurement chamber, and the measurement basin is arranged so that it can be removed from the lid for emptying, cleaning and filling.

11. The device according to claim 1, wherein electronic components of the computer sensitive to electromagnetic fields are arranged inside a shield constituted in the manner of a Faraday cage.

12. The device according to claim 11, wherein said device further comprise perforation in the shield provided for a cable lead-through provided on the side of the shield facing away from the igniter.

13. The device according to claim 12, wherein the case of a perforation provided on the side of the shield facing the igniter, the electronic components of the computer sensitive to electromagnetic fields are arranged outside the region of a cone with an opening angle of 30°, whose axis runs normal to the perforation and whose cone generatrices proceed from the edge of the perforation.

14. The device according to claim 13, wherein the lower opening angle is 84°.

15. The device according to claim 1, wherein electronic components of the computer sensitive to electromagnetic fields lie inside a region of a cone defined by a lower and an upper opening angle, the axis of said cone lying in the extension of the spark gap.

16. The device according to claim 15, wherein the lower opening angle amounts to 70° and the upper opening angle amounts to 90°.

17. The device according to claim 15, wherein the plane of the printed circuit board of the computer carrying the sensitive components is arranged at an angle of essentially 90° to the spark gap.

18. The device according to claim 15, wherein the sensitive components comprise a CPU, an analog-to-digital converter and/or an operational amplifier.

19. The device according to claim 15, wherein the lower opening angle amounts to 0° and the upper opening angle amounts to 40°.

20. The device according to claim 19, wherein the upper opening angle is 20°.

* * * * *